United States Patent
Yarden et al.

(10) Patent No.: US 9,926,564 B2
(45) Date of Patent: Mar. 27, 2018

(54) APTAMERS, MULTIMERIC APTAMERS AND USES THEREOF

(71) Applicant: Yeda Research and Development Co. Ltd., Rehovot (IL)

(72) Inventors: Yosef Yarden, Rehovot (IL); Michael Sela, Rehovot (IL); Georg Mahlknecht, Rehovot (IL); Ruth Maron, Rehovot (IL); Bilha Schechter, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/439,248

(22) PCT Filed: Oct. 27, 2013

(86) PCT No.: PCT/IL2013/050873
§ 371 (c)(1),
(2) Date: Apr. 29, 2015

(87) PCT Pub. No.: WO2014/068553
PCT Pub. Date: May 8, 2014

(65) Prior Publication Data
US 2015/0307883 A1    Oct. 29, 2015

Related U.S. Application Data

(60) Provisional application No. 61/719,596, filed on Oct. 29, 2012.

(51) Int. Cl.
*C07H 21/02* (2006.01)
*C07H 21/04* (2006.01)
*C12N 15/115* (2010.01)
*A61K 31/7088* (2006.01)
*G01N 33/574* (2006.01)
*C12N 5/00* (2006.01)

(52) U.S. Cl.
CPC ........ *C12N 15/115* (2013.01); *A61K 31/7088* (2013.01); *G01N 33/57492* (2013.01); *C12N 2310/16* (2013.01); *C12N 2310/351* (2013.01); *C12N 2310/3517* (2013.01); *C12N 2310/51* (2013.01); *C12N 2320/13* (2013.01); *C12N 2320/30* (2013.01); *C12N 2330/30* (2013.01); *G01N 2333/91205* (2013.01)

(58) Field of Classification Search
None
See application file for complete search history.

(56) References Cited

U.S. PATENT DOCUMENTS

| 6,458,559 B1 * | 10/2002 | Shi | C12N 15/115 435/320.1 |
| 2011/0275702 A1 | 11/2011 | Chang et al. | |
| 2012/0141382 A1 | 6/2012 | Shi et al. | |
| 2012/0190732 A1 | 7/2012 | Chang et al. | |
| 2012/0225088 A1 * | 9/2012 | Scheinberg | C12N 15/115 424/178.1 |
| 2013/0129719 A1 * | 5/2013 | Giangrande | C12N 15/1135 424/133.1 |
| 2014/0148501 A1 * | 5/2014 | Maher, III | A61K 38/17 514/44 R |

FOREIGN PATENT DOCUMENTS

| WO | WO 2011/006075 | 1/2011 |
| WO | WO 2012/049112 | 4/2012 |
| WO | WO 2013/025930 | 2/2013 |
| WO | WO 2014/068553 | 5/2014 |

OTHER PUBLICATIONS

Communication Relating to the Results of the Partial International Search dated Jan. 29, 2014 From the International Searching Authority Re. Application No. PCT/IL2013/050873.
International Preliminary Report on Patentability dated May 14, 2015 From the International Bureau of WIPO Re. Application No. PCT/IL2013/050873.
International Search Report and the Written Opinion dated Apr. 24, 2014 From the International Searching Authority Re. Application No. PCT/IL2013/050873.
Chen et al. "Inhibition of Heregulin Signaling by An Aptamer That Preferentially Binds to the Oligomeric Form of Human Epidermal Growth Factor Receptor-3", Proc. Natl. Acad. Sci. USA, PNAS, 100(16): 9226-9231, Aug. 5, 2003.
Dassie et al. "Systemic Administration of Optimized Aptamer-SiRNA Chimeras Promotes Regression of PSMA-Expression Tumors", Nature Biotechnology, 27(9): 839-849, Sep. 2009.
Dastjerdi et al. "Generation of An Enriched Pool of DNA Aptamers for An HER2-Overexpressing Cell Line Selected by Cell SELEX", Biotechnology and Applied Biochemistry, XP002715519, 58(4): 226-230, Aug. 16, 2011.
Esposito et al. "A Neutralizing RNA Aptamer Against EGFR Causes Selective Apoptotic Cell Death", PLoS ONE, 6(9): e24071-1-e24071-12, Sep. 2011.
Giangrande et al.
Kim et al. "In Vitro Selection of RNA Aptamer and Specific Targeting of ErbB2 in Breast Cancer Cells", Nucleic Acid Therapeutics, 21(3): 173-178, 2011.
Li et al. "Inhibition of Cell Proliferation by An Anti-EGFR Aptamer", PLoS One, 6(6): e20299-1-e20299-10, Jun. 2011.
Liu et al. "Novel HER2 Aptamer Selectively Delivers Cytotoxic Drug to HER2-Positive Breast Cancer Cells In Vitro", Journal of Translational Medicine, XP021107564, 10(148): 1-10, 2012.
Mahlknecht et al. "Aptamer to ErbB-2/HER2 Enhances Degradation of the Target and Inhibits Tumorigenic Growth", Proc. Natl. Acad. Sci. USA, PNAS, XP055097793, 110(2): 8170-8175, May 14, 2013.

(Continued)

*Primary Examiner* — Sean McGarry

(57) ABSTRACT

Monomeric and multimeric aptamers are provided. Also provided are pharmaceutical compositions which comprise same and methods of using same.

11 Claims, 8 Drawing Sheets
(8 of 8 Drawing Sheet(s) Filed in Color)

(56) References Cited

OTHER PUBLICATIONS

Shi et al. "RNA Aptamers as Effective Protein Antagonists in a Multicellular Organism", Proc. Natl. Acad. Sci. USA, XP002965808, 96(18): 10033-10038, Aug. 31, 1999.
Thiel et al. "Delivery of Chemo-Sensitizing SiRNAs to IIER2+-Breast Cancer Cells Using RNA Aptamers", Nucleic Acids Research, XP055097617, 40(13): 6319-6337, Mar. 30, 2012.
Communication Pursuant to Article 94(3) EPC dated Nov. 16, 2016 From the European Patent Office Re. Application No. 13792769.5.

* cited by examiner

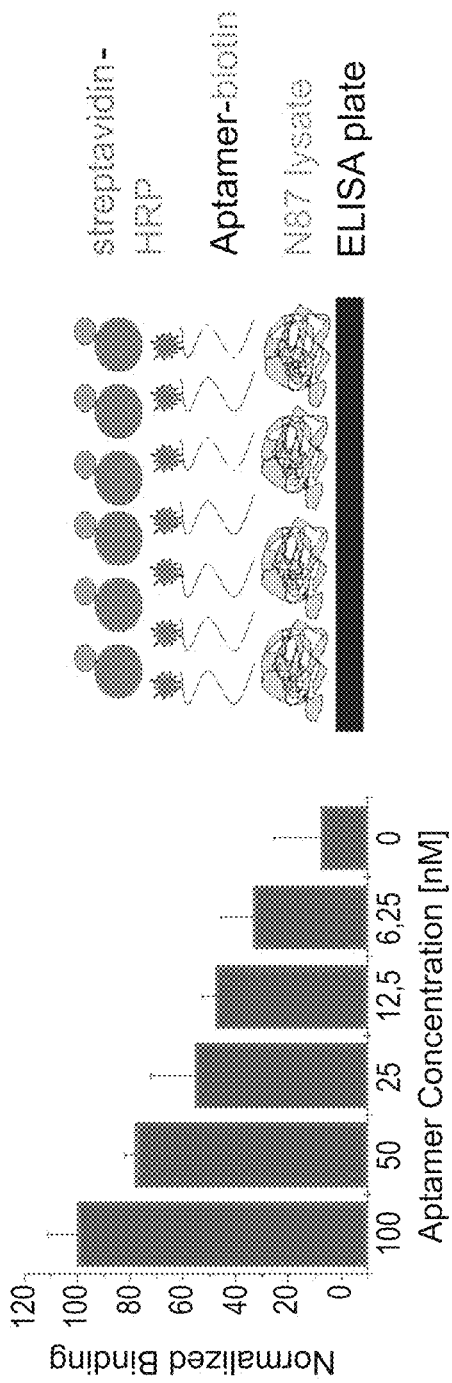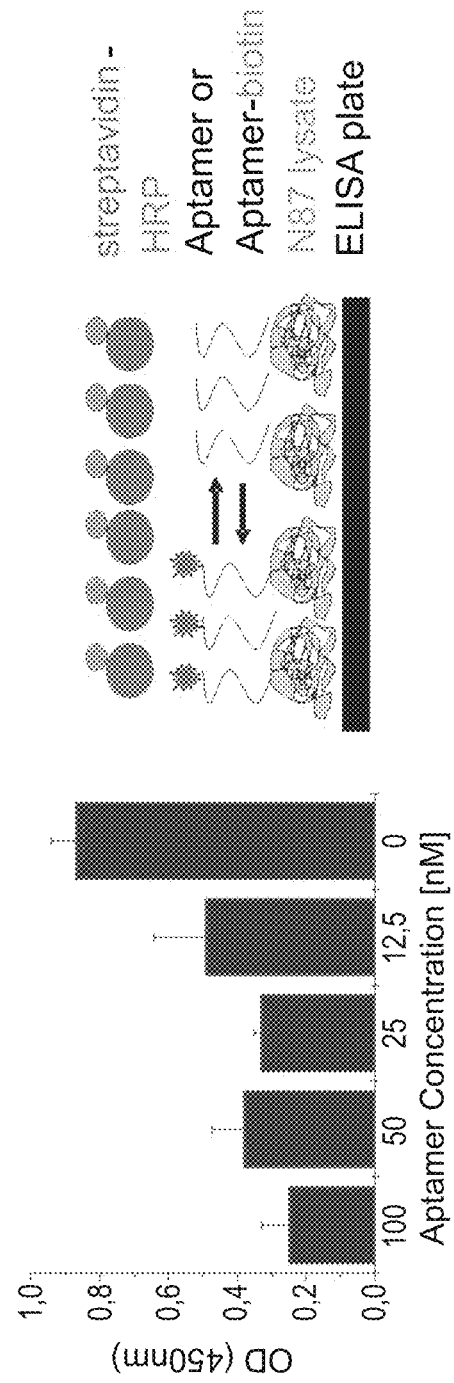
FIG. 2A
FIG. 2B

Oligonucleotide:   PR      B212    2-2     2-1

— 185 kDa

Cell line:  N87   N87   N87   N87        Cell line: A431 N87 A431 N87
Aptamer:    2-2         PR               Aptamer:   PR       2-2

— 185 kDa            — 185 kDa

APTAMERS, MULTIMERIC APTAMERS AND USES THEREOF

RELATED APPLICATIONS

This application is a National Phase of PCT Patent Application No. PCT/IL2013/050873 having International filing date of Oct. 27, 2013, which claims the benefit of priority under 35 USC § 119(e) of U.S. Provisional Patent Application No. 61/719,596 filed on Oct. 29, 2012. The contents of the above applications are all incorporated by reference as if fully set forth herein in their entirety.

STATEMENT REGARDING FEDERALLY SPONSORED RESEARCH OR DEVELOPMENT

This invention was made with government support under Contract No. CA072981 awarded by the NIH. The government has certain rights in the invention.

SEQUENCE LISTING STATEMENT

The ASCII file, entitled 62215SequenceListing.txt, created on Apr. 26, 2015 comprising 1,905 bytes, submitted concurrently with the filing of this application is incorporated herein by reference.

FIELD AND BACKGROUND OF THE INVENTION

The present invention, in some embodiments thereof, relates to aptamers, multimeric aptamers and uses thereof.

The ErbB family of receptor tyrosine kinases plays an important role in epitheliogenesis, and accordingly serves as a major therapeutic target in several cancers. The family comprises four transmembrane receptors and eleven ligands that induce homo- or heterodimerization upon binding to the respective receptor. ErbB-1 (also called the epidermal growth factor receptor; EGFR) and ErbB-4 share some ligands, whereas no similar ligand is so far known for ErbB-2. Overexpression and mutations of ErbB family members lead to a multitude of malignancies. To date, synthetic tyrosine kinase inhibitors (e.g., Erlotinib and Gefitinib), as well as monoclonal antibodies (mAbs; e.g., Cetuximab and Trastuzumab), have been developed to inhibit pathological signalling, or recruit the immune system to cancer cells. Aptamers might represent an alternative therapeutic modality. These are small, single-stranded DNA or RNA molecules. Aptamers are selected in an evolutionary process called SELEX (Systematic Evolution of Ligands by Exponential Enrichment). A DNA- or RNA-library containing single-stranded random sequences, flanked by two primer-binding regions, is allowed to bind to a specific target. In several selection rounds, binders are amplified and non-specific binders are removed in a partitioning step. Selected sequences can be modified after selection, to improve their stability in different chemical environments (e.g., serum). Different therapeutic aptamers, which are antiviral, anti-coagulation, anti-inflammatory or antiangiogenic, are already in clinical trials. The first clinically approved aptamer is an RNA-molecule, called Macugen, which effectively inhibits macular degeneration. In addition to pharmacological applications, aptamers can be exploited for transducing a binding event into a signal. As a consequence, aptamers have been adapted to a variety of bioanalytical methods.

Several anti-cancer aptamers have been developed, including an aptamer against Nucleolin, which led to phase 2 clinical trials. So far, several anti-ErbB-specific aptamers have been developed [Li N, Nguyen H H, Byrom M, & Ellington A D (2011) Inhibition of Cell Proliferation by an Anti-EGFR Aptamer. *PloS one* 6(6):e20299; Dastjerdi K, Tabar G H, Dehghani H, & Haghparast A (2011) Generation of an enriched pool of DNA aptamers for an HER2-over-expressing cell line selected by Cell SELEX. *Biotechnology and applied biochemistry* 58(4):226-230; Esposito C L, et al. (2011) A neutralizing RNA aptamer against EGFR causes selective apoptotic cell death. *PloS one* 6(9):e24071; Kim M Y & Jeong S (2011) In vitro selection of RNA aptamer and specific targeting of ErbB2 in breast cancer cells. *Nucleic acid therapeutics* 21(3):173-178; Chen C H, Chernis G A, Hoang V Q, & Landgraf R (2003) Inhibition of heregulin signaling by an aptamer that preferentially binds to the oligomeric form of human epidermal growth factor receptor-3. *Proceedings of the National Academy of Sciences of the United States of America* 100(16):9226-9231].

These aptamers generally show high affinity and specificity to their targets, and in the case of ErbB-1- and ErbB-3-specific aptamers, they also inhibit the proliferation of cultured cancer cells (Esposito et al. 2011, supra). Notably, an aptamer against ErbB-1/EGFR was able to inhibit tumor growth in a mouse model (Esposito et al. 2011 supra), and ErbB-2-specific aptamers were used to deliver siRNAs targeting Bcl-2 [Dassie J P, et al. (2009) Systemic administration of optimized aptamer-siRNA chimeras promotes regression of PSMA-expressing tumors. *Nature biotechnology* 27(9):839-849].

Additional background art includes:

U.S. Patent Application Number 20110275702 teaches a ligand-nucleic acid nanostructure that promotes cell-cell interaction. Specially, the ligand-nucleic acid nanostructure is a multimeric aptamer.

U.S. Patent Application Number 20120225088 teaches multimeric aptamers and methods of use.

U.S. Patent Application Number 20120190732 teaches a first ligand that is specific for binding to a tumor cell, and a second ligand that is specific for binding to a death receptor on the tumor cell, wherein the first and second ligands are bound to a nucleic acid nanostructure, wherein the first and second ligands are aptamers.

SUMMARY OF THE INVENTION

According to an aspect of some embodiments of the present invention there is provided a multimeric aptamer comprising a plurality of monomers, wherein at least one monomer of the plurality of monomers comprises a nucleic acid sequence capable of specifically binding an ErbB receptor molecule.

According to an aspect of some embodiments of the present invention there is provided an isolated aptamer comprising a nucleic acid sequence selected from the group consisting of SEQ ID NO: 1, 2 and 3.

According to an aspect of some embodiments of the present invention there is provided a multimeric aptamer comprising a plurality of monomers, wherein at least one monomer of the plurality of monomers is the aptamer above.

According to an aspect of some embodiments of the present invention there is provided an isolated aptamer comprising a nucleic acid sequence capable of specifically binding to, and inducing internalization of an ErbB receptor molecule.

According to some embodiments of the invention, the multimeric aptamer is devoid of spacers between the plurality of monomers.

According to some embodiments of the invention, the multispecific aptamer is a homomultimer.

According to some embodiments of the invention, the multispecific aptamer is a heteromultimer.

According to some embodiments of the invention, the multimeric aptamer is capable of inducing internalization of the ErbB receptor molecule.

According to some embodiments of the invention, the aptamer or multimeric aptamer is attached to a detectable moiety.

According to some embodiments of the invention, the aptamer or multimeric aptamer is attached to a therapeutic moiety.

According to an aspect of some embodiments of the present invention there is provided a pharmaceutical composition comprising as an active ingredient the multimeric aptamer or the aptamer described above and a pharmaceutically acceptable carrier or diluent.

According to an aspect of some embodiments of the present invention there is provided a method of detecting an expression of an ErbB receptor molecule on a cell, the method comprising:
(a) contacting the cell or a preparation thereof with the multimeric aptamer or the aptamer under conditions which allow complex formation between the ErbB receptor molecule and the multimeric aptamer or the aptamer;
(b) detecting a presence or level of the complex, thereby detecting expression of the ErbB receptor molecule.

According to an aspect of some embodiments of the present invention there is provided a method of delivering a therapeutic moiety to an ErbB expressing cell in a subject in need thereof, the method comprising administering to the subject a therapeutically effective amount of the aptamer or multimeric aptamer, thereby delivering the therapeutic moiety to the subject in need thereof.

According to an aspect of some embodiments of the present invention there is provided a method of killing or arresting growth of tumor cells overexpressing an ErbB receptor molecule in a subject in need thereof, the method comprising administering to the subject a therapeutically effective amount of the aptamer or multimeric aptamer, thereby killing or arresting growth of the tumor cells overexpressing an ErbB receptor molecule.

According to an aspect of some embodiments of the present invention there is provided a method of treating cancer in a subject in need thereof the method comprising administering to the subject a therapeutically effective amount of the aptamer or multimeric aptamer, thereby treating the cancer in the subject.

According to some embodiments of the invention, the ErbB receptor molecule comprises ErbB-2.

According to some embodiments of the invention, the method further comprises administering to the subject an anti-cancer therapy selected from the group consisting of a chemotherapy, a radiotherapy, a nucleic acid silencing agent and an antibody therapy.

According to an aspect of some embodiments of the present invention there is provided a multimeric aptamer comprising a plurality of monomers, wherein the multimeric aptamer is devoid of a spacer or spacers between the plurality of monomers.

According to some embodiments of the invention, each of the plurality of monomers is selected being of a functional length.

According to some embodiments of the invention, the functional length is 12-60 nucleotides.

According to some embodiments of the invention, the multispecific aptamer is a homomultimer.

According to some embodiments of the invention, the multispecific aptamer is a heteromultimer.

According to an aspect of some embodiments of the present invention there is provided multimeric aptamer as set forth in SEQ ID NO: 7.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
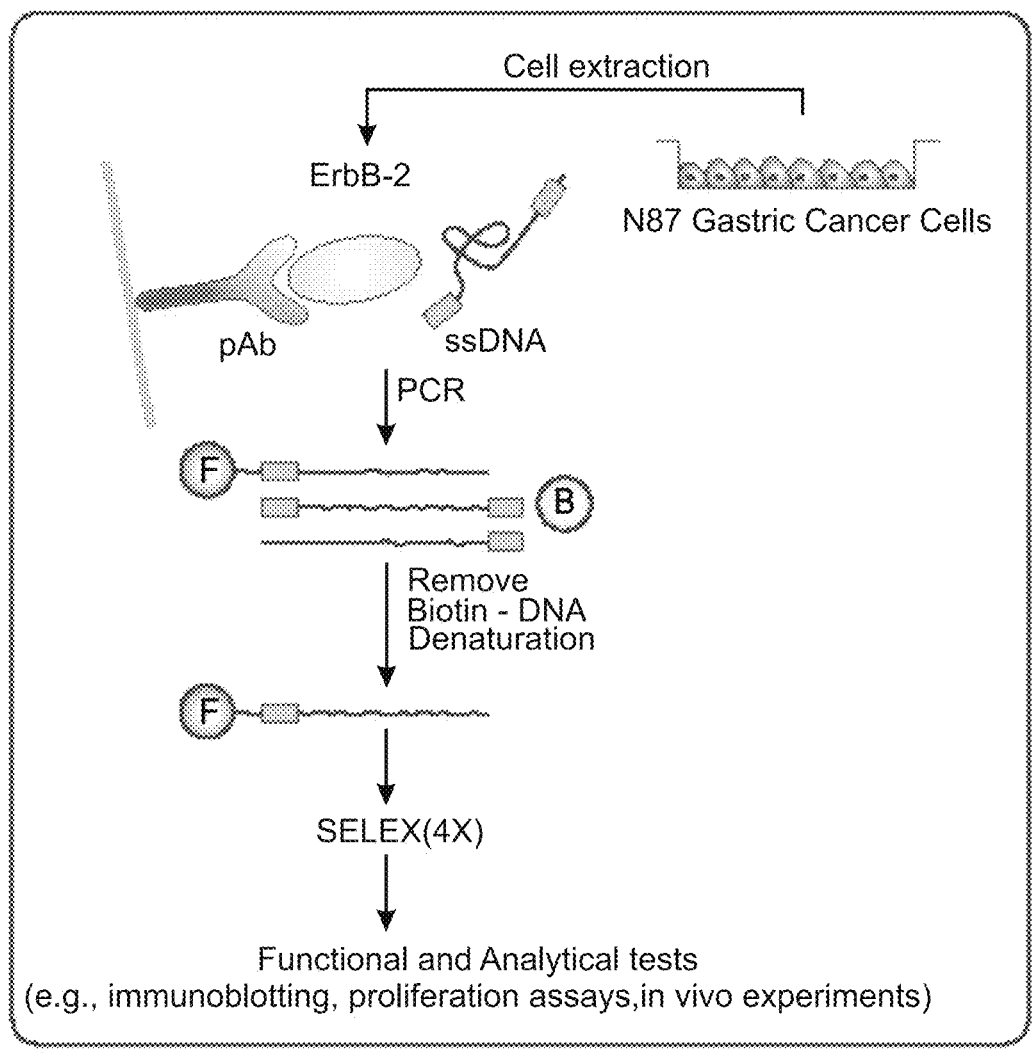

FIG. 1 is a graphic illustration of the SELEX protocol for selection of ErbB-2-specific aptamers. ErbB-2 was isolated from N87 gastric cancer cells using a polyclonal antiserum to the kinase domain. A library of single-stranded DNA aptamers was incubated with the antibody-ErbB-2 complexes, and then amplified by PCR. PCR amplification used a fluorescein-labelled primer for the leading strand, as well as a biotin-conjugated primer for the lagging strand. Double-stranded products of the PCR reaction were removed using streptavidin magnetic beads. In addition, the fluorescein label, which was released by heat denaturation, enabled quantification of PCR products after each round of selection. Five selection rounds were performed, including a fourth, counter selection step.

FIGS. 2A-B are illustrations confirming target specificity of aptamer 2-2. FIG. 2A—ErbB-2-specific, polyclonal rabbit antibody (0.1 µg/ml) was used to coat plate surfaces. After blocking with skim milk, cleared extracts from ErbB-2-overexpressing N87 cells (100 µg/ml) were added. Increasing concentrations of the biotinylated aptamer 2-2(t) (0-100 nM) or a control aptamer, PR(t), were allowed to bind to the immobilized ErbB-2. Streptavidin-conjugated HRP was used for detection. The data were normalized to the background binding of the trimeric control primer. The scheme on the right outlines the assay. FIG. 2B—A competition assay between a biotinylated, trimeric aptamer 2-2(t) and increasing concentrations of an unlabelled version of the same aptamer, was performed as in FIG. 2A. The scheme outlines the assay.

Figure 3A:
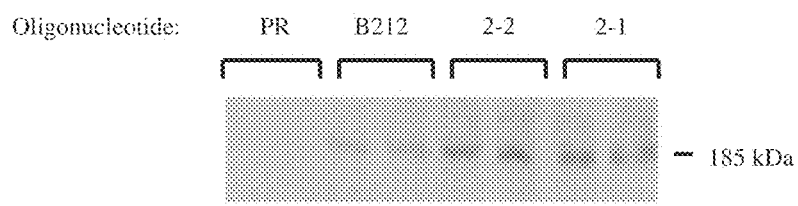
Figure 3B:
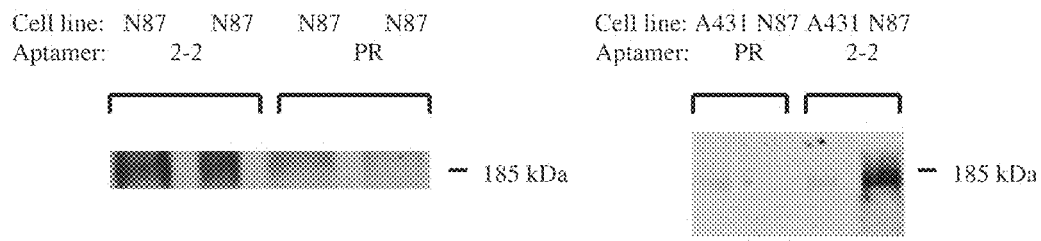

FIGS. 3A-B depict aptamer specificity to ErbB-2. FIG. 3A—Extracts of N87 cells were resolved by using gel electrophoresis, blotted onto a membrane, and after a blocking step the blot was incubated with the indicated biotinylated aptamers, along with the biotinylated primer (PR; each at 100 nM). Bound oligonucleotides were re-blotted to a second membrane and detected with HRP-labelled streptavidin. FIG. 3B—Biotinylated aptamers 2-2 and the control primer (PR) were immobilized on streptavidin beads and used to pull-down ErbB-2 from extracts of N87 cells (500 µg/ml). For control extracts of A431 cells were used. Pull-downs were resolved using gel electrophoresis, blotting to a nitrocellulose membrane and ErbB-2 detection with a rabbit polyclonal antiserum to the kinase domain. Colorimetric immunostaining was achieved with an HRP-labelled secondary antibody.

Figure 4A:
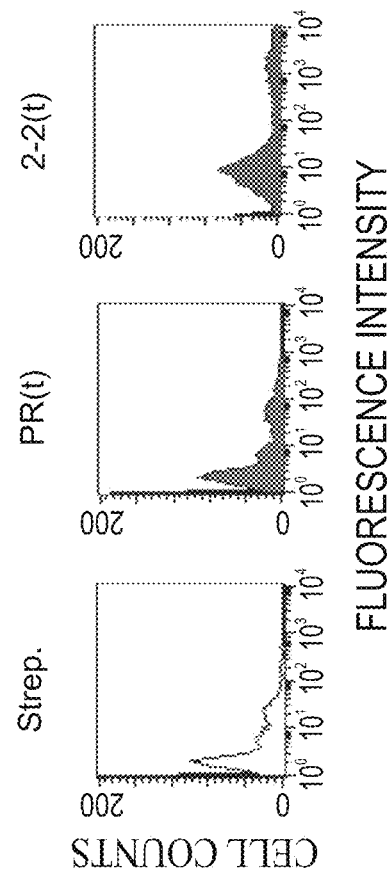
Figure 4B:
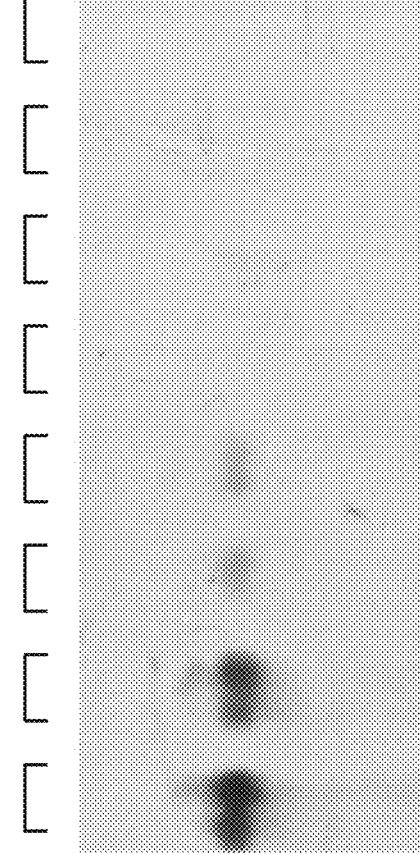
Figure 4C:
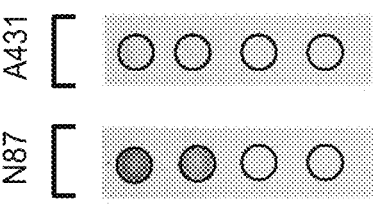

FIGS. 4A-C display improved ErbB-2 binding of a trimeric aptamer. FIG. 4A—Whole extracts were prepared from ErbB-2-overexpressing N87 cells and ErbB-1-overexpressing A431 cells. Samples (10 µg) were spotted onto a nitrocellulose membrane. Biotinylated trimeric (2-2(t)) or monomeric aptamers, each at 100 nM, were applied in duplicates. HRP-labelled streptavidin was used for detection. FIG. 4B—N87 cells were treated with trypsin, washed and incubated at 4° C. for 30 min with aptamers 2-2(t) or PR(t) in saline containing 0.1% albumin Thereafter, cells were washed and conjugated streptavidin was added at 4° C. for 30 min. Fluorescence was measured using FACSORT cytometer. FIG. 4C—The indicated biotinylated aptamers (1 µM) were conjugated to magnetic beads and incubated with extracts (500 µg/ml) from N87 or A431 cells. Extensively washed precipitates were separated using gel electrophoresis, and then blotted onto a nitrocellulose membrane. The membrane was blocked and probed with an ErbB-2-specific polyclonal antiserum, followed by an HRP-labelled secondary antibody.

Figure 5:
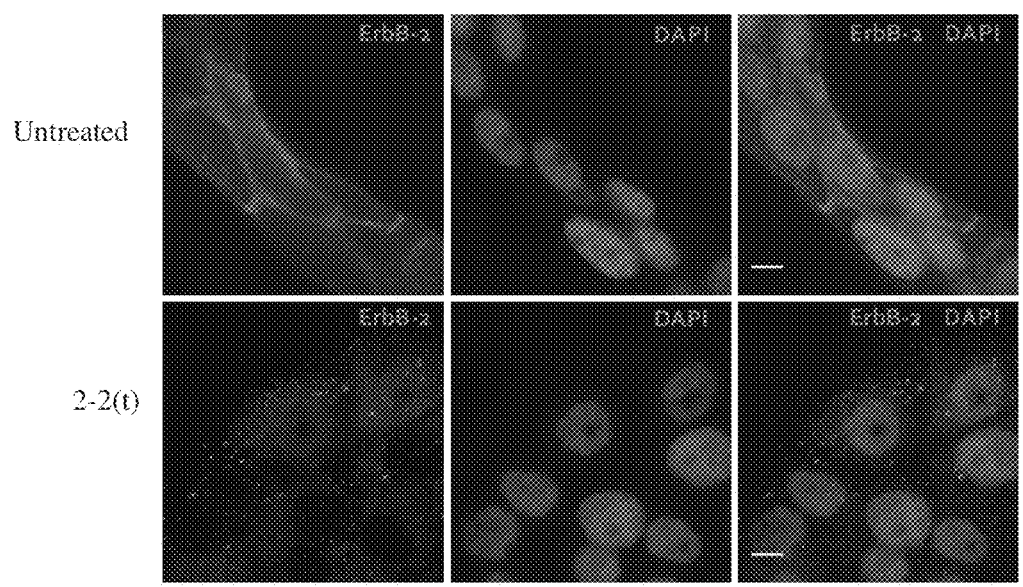

FIG. 5 images that the trimeric aptamer promotes translocation of surface ErbB-2 into intracellular puncta. N87 cells growing on fibronectin were treated with the trimeric aptamer 2-2 (SEQ ID NO: 2) (100 nM) for three days Immunofluorescence localization of ErbB-2 employed a rabbit antibody, as well as a secondary, fluorescently labelled antibody. DAPI was used to visualize nuclei. Scale bar, 5 µm.

Figure 6A:
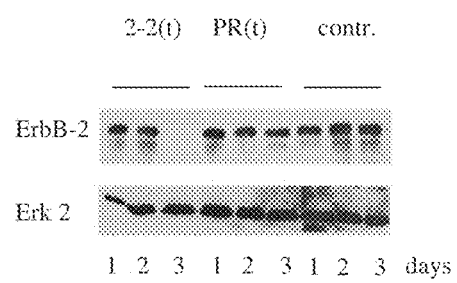
Figure 6B:
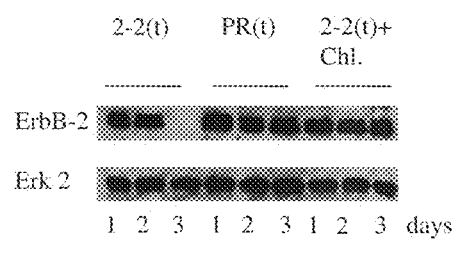

FIGS. 6A-B show that the trimeric aptamer 2-2 (SEQ ID NO: 2) enhances lysosomal degradation of ErbB-2. FIG. 6A—N87 cells ($10^5$) were plated on 24-well plates and incubated for 1-3 days with the trimeric aptamer 2-2(t) (10 µM), or with the trimeric primer PR(t). Thereafter, cells were extracted and subjected to electrophoresis and immunoblotting with an ErbB-2-specific polyclonal antiserum. Antibodies to ERK were used to test equal loading, and HRP-labelled secondary antibodies were used for detection. FIG. 6B—Cells were treated with aptamers as in A, except that chloroquine (Chl.; 0.01 µM) was co-incubated with the aptamer.

Figure 7A:
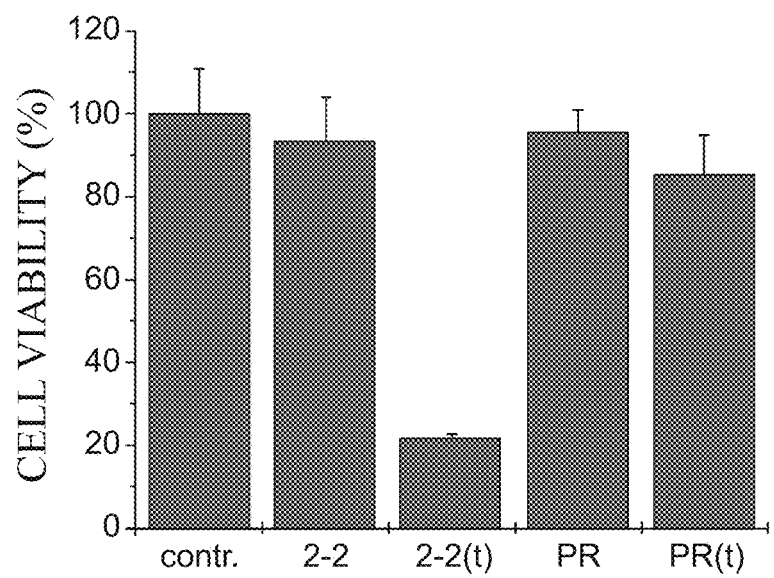
Figure 7B:
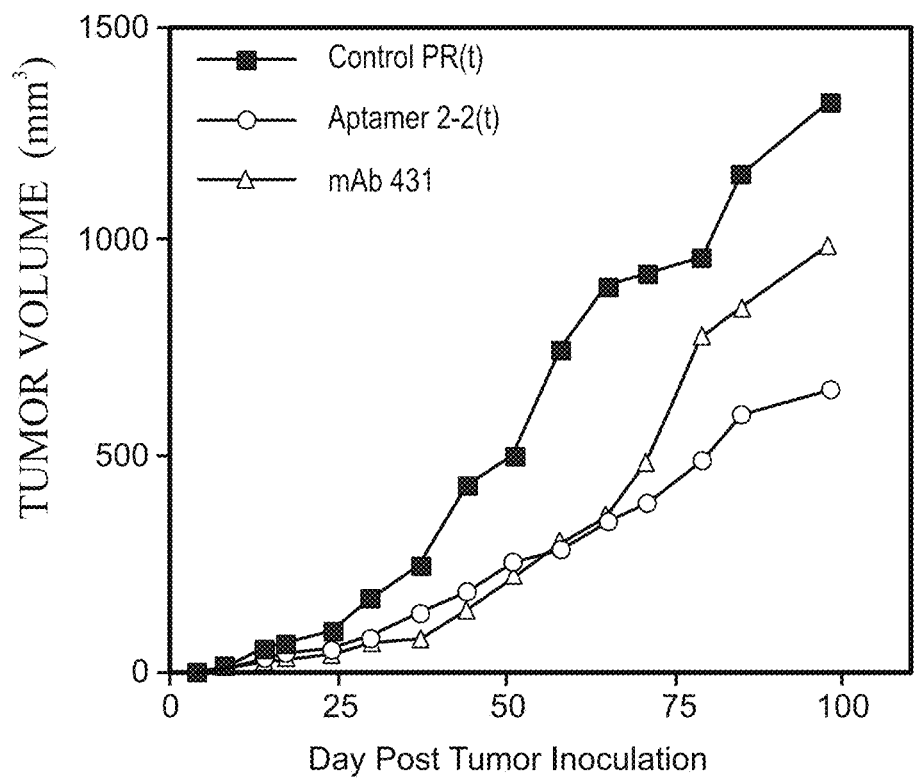

FIGS. 7A-B are graphs showing that the trimeric aptamer inhibits growth of gastric cancer cells both in vitro and in animals. FIG. 7A—N87 cells ($10^3$ cells/well) were plated on 96-well plates and 24 hours later monomeric (2-2 and PR) or trimeric aptamers (2-2(t) and PR(t)) at 10 µM were added. Subsequently, cells were incubated at 37° C. for 7 days, and the medium was refreshed on every other day. Cell proliferation was determined using a commercial kit. FIG. 7B—CD-1 nude mice (7 per group) were inoculated with $5\times10^6$ N87 cells. Once tumors became palpable, mice were treated intraperitoneally, once per week (for 8 times) with the ErbB-2-specific mAb431 (160 µg/week), the trimeric, ErbB-2-specific aptamer 2-2(t) or with PR(t) (40 µg/week). Untreated tumor-bearing mice were similarly monitored; their rate of tumor growth was statistically indistinguishable from the rate displayed by the PR(t)-treated group. Shown are the results of one of three experiments.

Figure 8:
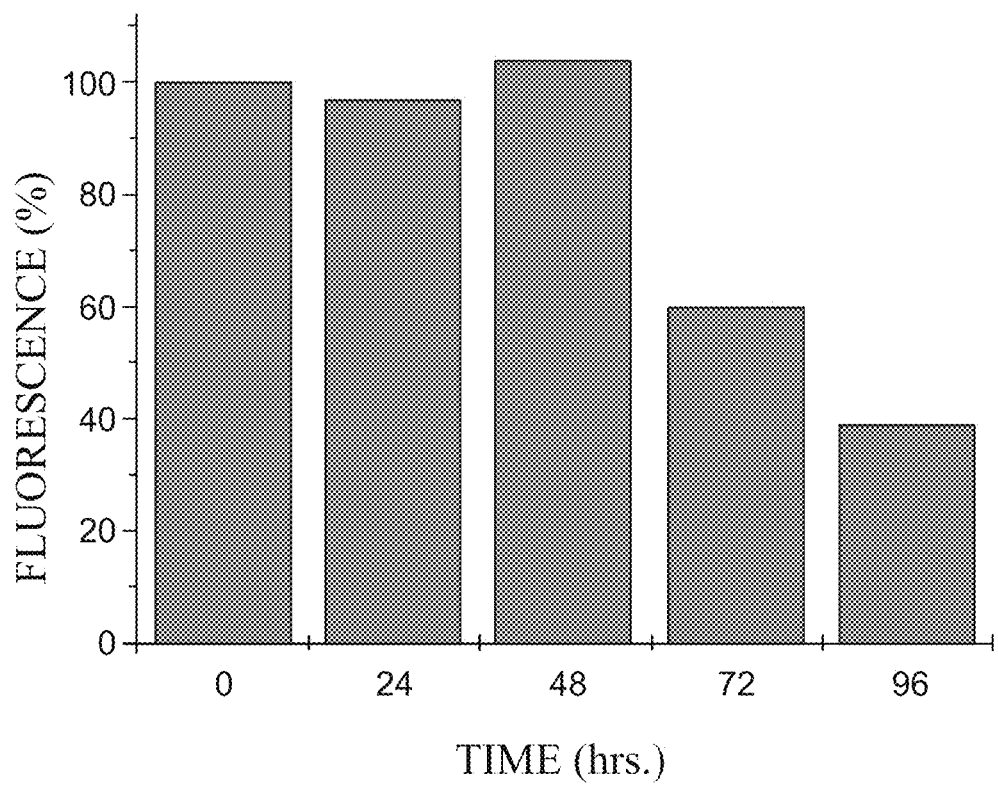

FIG. 8 shows that the trimeric aptamer 2-2(t) is stable for two days in serum. A fluorescein-labelled trimeric aptamer 2-2(t) (10 µM) was incubated at 37° C. for up to 96 hours in mouse serum (diluted 1:1 with saline). At the indicated time intervals, samples were removed and frozen at −20° C. Thereafter, all samples were subjected to PCR with the primers used for the SELEX selection rounds. Double-stranded PCR products containing the fluorescein label in the leading strand and a biotin label in the lagging strand were incubated with streptavidin magnetic beads. Subsequently, the fluorescein labelled leading strand was released and fluorescence intensity was measured.

DESCRIPTION OF SPECIFIC EMBODIMENTS OF THE INVENTION

The present invention, in some embodiments thereof, relates to aptamers, multimeric aptamers and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing the present invention to practice, the present inventors have selected through laborious experimentation and screening a plurality of aptamers specifically recognizing ErbB-2/HER2, a receptor tyrosine kinase, which is overexpressed in a variety of human cancers, including breast and gastric tumors (Example 2). Treatment of human gastric cancer cells with a trimeric version of the selected aptamer resulted in reduced cell growth in vitro, but a monomeric version was ineffective (Examples 2 and 5). Likewise, when treated with the trimeric aptamer, animals bearing tumor xenografts of human gastric origin reflected reduced rates of tumor growth. The anti-tumor effect of the aptamer exceeded that of a monoclonal anti-ErbB-2/HER2 antibody (Example 5). Consistent with aptamer-induced intracellular degradation of ErbB-2/HER2, incubation of gastric cancer cells with the trimeric aptamer promoted translocation of ErbB-2/HER2 from the cell surface to cytoplasmic puncta (Example 4). This shift was associated with a lysosomal hydrolase-dependent clearance of the ErbB-2/HER2 protein from cell extracts. It is concluded that targeting ErbB-2/HER2 with DNA aptamers might retard the tumorigenic growth of cancer (e.g., gastric cancer) by means of accelerating lysosomal degradation of the oncoprotein. This work exemplifies the potential pharmacological utility of aptamers directed at cell surface proteins, and it highlights an endocytosis-mediated mechanism of tumor inhibition.

Thus, according to the invention there are provided monomeric and multimeric aptamers, which are capable of binding an ErbB receptor molecule.

According to an aspect of the invention, there is provided a multimeric aptamer comprising a plurality of monomers, wherein at least one monomer of said multimeric aptamer comprises a nucleic acid sequence capable of specifically binding an ErbB receptor molecule.

According to another aspect there is provided an isolated aptamer comprising a nucleic acid sequence selected from the group consisting of SEQ ID NO: 1, 2 and 3 (B212, 2-2 and 2-1, respectively).

According to yet another aspect there is provided a multimeric aptamer comprising a plurality of monomers, wherein at least one monomer of said plurality of monomers comprises a nucleic acid sequence selected from the group consisting of SEQ ID NO: 1, 2 and 3 (B212, 2-2 and 2-1, respectively).

According to still another aspect, there is provided an isolated aptamer comprising a nucleic acid sequence capable of specifically binding to, and inducing internalization of an ErbB receptor molecule.

As used herein "an ErbB receptor molecule" refers to a receptor of the ErbB family of four structurally related receptor tyrosine kinases. In humans this includes Her1 (EGFR, ErbB-1), Her2 (Neu, ErbB-2), Her3 (ErbB-3), and Her4 (ErbB-4). According to a specific embodiment, the ErbB receptor molecule is ErbB-2.

The term "aptamer" as used herein refers to single-stranded nucleic acid molecules with secondary structures that facilitate high-affinity binding to a target molecule. In certain embodiments, the single-stranded nucleic acid is ssDNA, RNA or derivatives thereof to improve bioavailability. Aptamer binding affinity to the target protein is further described hereinbelow.

The aptamer of some embodiments of the invention is isolated. As used herein the term "isolated" refers to at least partially purified from a physiological environment e.g., serum, blood or tissue.

According to an embodiment of the invention, the aptamer is a monomer (one unit).

According to another embodiment of the invention, the aptamer is a multimeric aptamer. The multimeric aptamer may comprise a plurality of aptamer units (mers). Each of the plurality of units of the aptamer may be identical. In such a case the multimeric aptamer is a homomultimer having a single specificity but enhanced avidity (multivalent aptamer).

Alternatively, the multimeric aptamer may comprise two or more aptameric monomers, wherein at least two mers of the multimeric aptamer are non-identical in structure, nucleic acid sequence or both. Such a multimeric aptamer is referred to herein as a heteromultimer. The heteromultimer may be directed to a single binding site i.e., monospecific (such as to avoid steric hindrance). The heteromultimer may be directed to a plurality of binding sites i.e., multispecific. The heteromultimer may be directed to a plurality of binding sites on different ErbB members (e.g., ErbB-2 and ErbB-3; or ErbB-1 and ErbB-2; or ErbB-2 and ErbB-4; or ErbB-1 and ErbB-4). The heteromultimer may be directed to an ErbB protein (e.g., ErbB-2) and another cell surface protein (e.g., ErbB-2 and CD86) or specifically, another receptor tyrosine kinase (e.g., HGFR, FGFR or PDGFR). Further description of the multimeric aptamer is provided hereinbelow.

A plurality of multimeric aptamers may be conjugated to form a conjugate of multimeric aptamers.

The multimeric aptamer may comprise, two (dimer), three (trimer), four (tetramer), five (pentamer), six (hexamer), and even more units.

According to a specific embodiment the multimeric aptamer is as set forth in SEQ ID NO: 7 (GCAGCGGTGT GGGGGCAGCGGTGT GGGGGCAGCGGTGTGGGG).

As mentioned, according to a specific embodiment of the invention, the monomeric aptamer or the multimeric aptamer is capable of binding an ErbB receptor molecule.

As used herein, the term "capable of specifically binding to an ErbB receptor molecule" refers to direct binding of the aptamer (monomeric or multimeric) to the ErbB receptor molecule with a higher affinity than to a non-ErbB receptor molecule. An exemplary range for higher affinity refers to $10^2$-$10^5$ fold higher binding. According to a specific embodiment, the aptamer is capable of specifically binding a single ErbB receptor molecule (e.g., ErbB-2), essentially binding with a lower affinity to other members of the ErbB receptor family (e.g., ErbB-1, ErbB-3 and ErbB-4). Lower affinity in this context refers to e.g., $10^2$-$10^5$, $10^2$-$10^3$ fold lower binding affinity. Such a mode of binding is referred to herein as non-cross reactive. Conversely, the aptamer is capable of specifically binding two or more members of the ErbB receptor molecule (e.g., ErbB-2 and ErbB-3). Such aptamers are considered pan-ErbB or cross-reactive.

Methods of analyzing binding affinity are well known in the art and include, but are not limited to Biacore, Scatchard analysis and more.

As mentioned, any of the aptamers of the present invention can bind an ErbB receptor molecule and induce internalization (endocytosis) and optionally degradation of same. For example, as shown hereinbelow, the trimeric aptamer 2-2(t) effectively targeted ErbB-2 to intracellular lysosomal-dependent degradation. For other ErbB receptor molecules, other modes of degradation can be envisaged e.g., ubiquitin-dependent degradation.

As used herein the term "internalization" refers to the removal of specific proteins (e.g., ErbB) from the cell surface.

Internalization according to the present invention preferably results in receptor degradation which may be ubiquitin (as well as c-Cbl) dependent or independent.

As used herein the phrase "synergistic endocytosis" refers to the ability of the multimeric aptamer of a combination of monomeric aptamers to remove the target ErbB from the cell-surface in a total effect that is greater than the sum of the individual effects of each individual mer.

Methods of detecting lysosomal degradation/ubiquitin-dependent degradation of ErbB receptor molecules are well known in the art and described hereinbelow and in Klapper et al. (2000) Cancer Research 60(13):3384-3388.

As mentioned, the aptamer comprises a nucleic acid sequence.

As used herein, the terms "polynucleotide", "nucleotide", "oligonucleotide", and "nucleic acid" may be used interchangeably to refer to nucleic acid comprising DNA, RNA, derivative thereof, or combination thereof.

Thus, the "nucleic acid" according to embodiments of the invention may refer to DNA, RNA, peptide nucleic acids ("PNA"), and locked nucleic acids ("LNA"), nucleic acid-like structures, as well as combinations thereof and analogues thereof, unless specifically indicated. Nucleic acid analogues include known analogues of natural nucleotides which have similar or improved binding properties. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993)

J. Med. Chem. 36:1923-1937; Antisense Research and Applications (1993, CRC Press).

Aptamers of the invention can be synthesized and screened by any suitable methods in the art. Example 1 outlines a strategy for the isolation of an aptamer according to the teachings of the present invention and is hereby generalized to the present teachings.

For example, aptamers can be screened and identified from a random aptamer library by SELEX (systematic evolution of ligands by exponential enrichment). Aptamers that bind to an ErbB receptor molecule (e.g., ErbB-2) displayed on a cell surface (e.g., N87) can be suitably screened and selected by a modified selection method herein referred to as cell-SELEX or cellular-SELEX [Dastjerdi et al. 2011 Biotechnology and applied biochemistry 58(4):226-230; Phillips et al., 2008, Anal Chim Acta 621:101-108; Shamah et al., 2008, Acc Chem Res 41:130-138]. In certain other embodiments, aptamers that bind to a cell surface target molecule (e.g., an ErbB receptor molecule) can be screened by capillary electrophoresis and enriched by SELEX based on the observation that aptamer-target molecule complexes exhibited retarded migration rate in native polyacrylamide gel electrophoresis as compared to unbound aptamers.

In certain embodiments, a random aptamer library can be created that contains monomeric, dimeric, trimeric, tetrameric or other higher multimeric aptamers. A random aptamer library (either ssDNA or RNA) can be modified by including oligonucleotide linkers to link individual aptamer monomers to form multimeric aptamer fusion molecules. In certain embodiments, a random oligonucleotide library is synthesized with randomized 45 nt sequences flanked by defined 20 nt sequences both upstream and downstream of the random sequence, i.e., known as 5'-arm and 3'-arm, which are used for the amplification of selected aptamers. A linking oligonucleotide (i.e., linker) is designed to contain sequences complementary to both 5'-arm and 3'-arm regions of random aptamers to form dimeric aptamers. For trimeric or tetrameric aptamers, a small trimeric or tetrameric (i.e., a Holiday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors. Alternatively, multimeric aptamers can also be formed by mixing biotinylated aptamers with streptavidin.

A modified cellular SELEX procedure can be employed to select target-binding aptamers. As mentioned, multimeric aptamers may be multivalent but be of single binding specificity (i.e., homomultimeric aptamers). Alternatively, the multimeric aptamer may be multivalent and multi-specific (i.e., heteromultimeric aptamers).

Thus, each monomer of the homomultimeric aptamer binds the target protein (e.g., ErbB-2) in an identical manner. Thus according to an embodiment of the invention, all monomeric components of the homomultimeric aptamer are identical.

Conversely, a heteromultimeric aptamer comprises a plurality of monomeric aptamers at least two of which bind different sites on a single target protein [e.g., (hetero) dimerization domain of ErbB-2 and EGF-domain of ErbB-2] or bind at least two different target proteins (e.g., ErbB-1 and ErbB-2; or ErbB-2 and ErbB-3).

For selection of RNA-aptamers, a well-established RNA-aptamer selection protocol (Ohuchi et al., 2006. Biochimie 88:897-904) is applied with some modification. The dsDNA after PCR amplification of the random DNA library is transcribed to generate a RNA pool using T7-RNA polymerase. This RNA library is optionally incubated with linkers to form multivalent aptamer library. The aptamers from the library are incubated with target tumor cells expressing the ErbB receptor molecule(s) and counter-selected against normal cells or other non-target tumor cells. The selected RNA aptamers are reversely transcribed into cDNA and amplified by PCR, which will then be transcribed into RNA. These RNA molecules can be incubated with linkers to form multivalent aptamers for the next round of selection and amplification. Aptamers of ssDNA or RNA aptamers labeled with fluorophore can be used to reveal aptamer-specific cell binding by flow cytometry. Furthermore, the aptamers specific for an ErbB receptor molecule can also be enriched through FACS-based cell sorting. After 20-30 cycles of positive/negative selection, the selected aptamers can be cloned and sequenced. The binding valence and specificity of selected multimeric aptamer can be further characterized. For example, the binding aptamers can be eluted from the cells and analyzed by gel electrophoresis for the size and species, some of which will be analyzed by sequence analyses.

In certain embodiments, a suitable nucleotide length for an aptamer ranges from about 15 to about 100 nucleotide (nt), and in various other embodiments, 12-30, 14-30, 15-30 nt, 30-100 nt, 30-60 nt, 25-70 nt, 25-60 nt, 40-60 nt, or 40-70 nt in length.

In certain embodiments, the aptamer has affinity at the range of 10-100 nM, which, after binding of the aptamer to a tumor cell surface molecule, permits dissociation of the aptamer from the target molecule (e.g., ErbB receptor molecule), which leads to the release and recycle of the aptamer nucleic acid nanostructure to target other tumor cells. The affinity of individual aptamers can be increased by 4-50 fold by constructing multimeric aptamers linked together by covalent or non-covalent linkages. Methods of multimerizing aptamers are further described hereinbelow.

Thus, in certain embodiments, the desirable affinity of an aptamer to a target death receptor (e.g., ErbB receptor molecule) can be fine-tuned by adjusting the multiplicity of the monomeric aptamer.

Multimerization can be done at the library level as follows.

In certain embodiments, a linker polynucleotide has a length between about 5 nucleotides (nt) and about 100 nt; in various embodiments, 10-30 nt, 20-30 nt, 25-35 nt, 30-50 nt, 40-50 nt, 50-60 nt, 55-65 nt, 50-80 nt, or 80-100 nt. It is within the ability of one of skill in the art to adjust the length of the linker polynucleotide to accommodate each monomeric aptamer in the multimeric structure.

In certain embodiments, the multimeric aptamers can be identified and screened from a random multimeric aptamer library as described herein. In other embodiments, the monomeric aptamers are linked to each other by one or a plurality of linker polynucleotides to form multimeric aptamers. Monomeric aptamers can be linked to form multimeric aptamers by any suitable means and in any configurations.

In certain embodiments, the monomeric aptamer comprises a first portion of a randomized sequence that is about 25 to 100 nucleotide (nt) in length, and in various other embodiments, 30-100 nt, 30-60 nt, 25-70 nt, 25-60 nt, 40-60 nt, or 40-70 nt in length. In certain embodiments, the randomized sequence is 45 nt in length.

In other embodiments, the randomized sequence is flanked by at least one preferably two, predetermined sequences of about 10-50 nt in length, and in various other embodiments, 15-40 nt, 15-30 nt, 20-40 nt, 25-30 nt, or 20-30 nt in length.

In certain embodiments, the predetermined sequence is 20 nt in length. In certain embodiments, each monomeric aptamer comprises a randomized 45 nt sequence flanked by defined 20 nt sequences both upstream and downstream of the random sequence, i.e., the 5'-arm and 3'-arm, respectively. Computer programs are available to assist in designing the suitable predetermined sequence of the 5'-arm and 3'-arm regions to facilitate hybridization with the linker polynucleotide and to minimize potential secondary structure in the 5'-arm and 3'-arm regions. Exemplary computer program includes without limitation Mfold available at web site mobyle(dot)pasteurfecgi-bin/MobylePortal/portal(dot)py?form=mfold.

In certain embodiments of this aspect, randomized dimeric aptamers are formed wherein a linker polynucleotide comprises sequences complementary to both 5'-arm and/or 3'-arm region of random aptamers to form dimeric aptamers. In other embodiments, trimeric or tetrameric aptamers are formed when a plurality of linker polynucleotides that hybridize to the 3'-arm and 5'-arm regions are introduced. In other embodiments, the linker polynucleotide further comprises a single stranded hinge region situated in between the aptamer-binding motifs. In certain embodiments, the hinge region is 3-10 nt in length; in various other embodiments, the hinge region is 3-8 nt, 3-6 nt or 3-5 nt in length. In other embodiments, the hinge region comprises sequence that is rich in As and Ts. The additional single stranded hinge region offers flexibility to allow the multimeric aptamers to coordinate and synergize multivalent interactions with target molecules or receptors.

As used herein, the term "randomized sequence" refers to an undefined nucleic acid molecule that contains degenerative nucleotide residues at some or all positions. Nucleic acid containing randomized sequence can be chemically synthesized by various methods known in the art and described herein.

As used herein, the term "predetermined sequence" refers to a defined nucleic acid molecule for which the nucleotide sequence is known. Nucleic acid containing randomized sequence can be chemically synthesized by methods known in the art and described herein or produced recombinantly in a cell.

In certain embodiments, the predetermined sequence is complementary to at least 10 nt of sequence of the linker polynucleotide; in various other embodiments, at least 15 nt, 20 nt, 25 nt, 30 nt, 35 nt, 40 nt, 45 nt or 50 nt of the sequence of the linker polynucleotide.

It will be appreciated that the monomeric structures of the invention can be further multimerized by post SELEX procedures.

Multimers can be linearly linked by continuous linear synthesis of DNA without spacers (as described herein, see Examples section) or with nucleic acid spacers. Aptamer synthesis usually relies on standard solid phase phosphoramitide chemistry.

Thus, dimers, trimers and tetramers or higher oligomeric structures (e.g., pentamers, hexamers, heptamers, octamers etc.) can be linked by a polymeric spacer. Methods of generating such polymeric structures are provided in details in U.S. Patent Application 20120225088 which is hereby incorporated by reference in its entirety.

The preparation of the monomeric and multimeric aptamers embodied herein as well as the methods for their evaluation in vitro and in vivo can be achieved by following the descriptions provided herein including those in the examples below, as well as in the literature referred to herein which is fully incorporated herein by reference. For example, DNA oligonucleotide sequences can be chemically synthesized using standard solid phase phosphoramidite chemistry on, for example, an ABI394 DNA synthesizer using either a 0.2 μmole or 1 mole scale. Synthesis can include attaching a fluorophore at the 5' end. The completed DNA sequences are then de-protected, and the crude product purified using, for example HPLC (Beckman Coulter System Gold Bioessential 125/168 diode-array detection instrument) equipped with a C-18 column (Dyanamax 250 times 10 mm, Varian) using 0.1 M TEAA as the mobile phase. The length of each DNA construct can be confirmed using 10%-TBE urea polyacrylamide gel electrophoresis. Full length DNA can be quantified by measuring the absorbance at 260 nm and absorbance of the corresponding dye at the 5' position using a Cary Bio-100 UV-Visible spectrophotometer (Varian). Sequences used in NMR experiments can be further dialyzed overnight with 0.5 mM $NaHPO_4$ buffer using a MWCO 1000 Da dialysis bag.

In certain embodiments, the aptamers are further modified to protect the aptamers from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamer. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants (Epicentre Biotech, Madison, Wis.). The resistance of these modified aptamers to nuclease can be tested by incubating them with either purified nucleases or nuclease from mouse serum, and the integrity of aptamers can be analyzed by gel electrophoresis.

The monomeric or multimeric aptamer of the invention can be further attached or conjugated to a detectable or therapeutic moiety (i.e., a pharmaceutical moiety).

However, it will be appreciated that the attachment of a therapeutic moiety is not crucial since the aptamers of the invention are endowed with an intrinsic cell growth inhibitory activity. As shown in FIGS. 7A-B the aptamer of one embodiment of the invention inhibits growth of cancer cells in-vitro and in-vivo.

Thus, as noted above, a diagnostic or therapeutic moiety can be attached to an aptamer embodied herein to provide additional biological activity, such as for diagnosing, preventing, or treating a condition or disease. In one embodiment a diagnostic moiety such as a detectable moiety e.g., label (e.g., His tag, flag tag), fluorescent, radioactive, biotin/avidin etc., can be bound to the aptamer, and imaging, immunohistochemistry, or other invasive or non-invasive methods used to identify the location(s) and extend of binding of the conjugate to locations within the body.

For therapeutic uses, a cytotoxic agent such as a chemotherapeutic agent, radioactive moiety, toxin, antibody, nucleic acid silencing agents e.g., small interfering RNA (siRNA) or other molecule with therapeutic activity when delivered to cells expressing a molecule to which the aptamer is targeted, may be used to enhance the therapeutic activity of the aptamer or provide a biological activity where the aptamer is providing the targeting activity. Moreover, other conjugates to the aptamers described herein are contemplated, such as but not limited to scaffolds, sugars, proteins, antibodies, polymers, and nanoparticles, each of which have art-recognized therapeutic or diagnostic utilities and can be targeted to particular sites in vivo using an aptamer embodied herein.

Thus, since the aptamers of the invention are capable of specifically binding an ErbB receptor molecule, they may be used in diagnostic applications.

Thus, there is provided a method of detecting an expression of an ErbB receptor molecule on a cell, the method comprising:
(a) contacting the cell or a preparation thereof with the multimeric aptamer or the aptamer described herein under conditions which allow complex formation between the ErbB receptor molecule and the multimeric aptamer or the aptamer;
(b) detecting a presence or level of said complex, thereby detecting expression of said ErbB receptor molecule.

To simplify, for such applications, the aptamer is attached (directly or indirectly conjugated to a detectable moiety). The imaging method is selected based on the identity of the conjugated detectable moiety.

Such teachings can be further implemented in diagnostic applications.

Thus, according to an aspect of the invention there is provided a method of diagnosing a medical condition (e.g., tumor) characterized by cells overexpressing an ErbB receptor molecule.

As used herein "overexpressing" refers to the protein level of the ErbB receptor molecule in the cell which is higher than that found in a corresponding cell of a normal unaffected, healthy (e.g., non-transformed/non-malignant) tissue of the same origin.

As used herein the term "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

According to some embodiments of the invention, screening of the subject for a specific disease is followed by substantiation of the screen results using gold standard methods.

A variety of medical conditions are associated with ErbB receptor molecule overexpression or disregulated activity. Examples include but are not limited to schizophrenia, restenosis, arthritis and hyperproliferative diseases such as psoriasis. Of special note is cancer.

Non-limiting examples of cancers which can be diagnosed and treated according to some embodiments of the invention can be any solid or non-solid cancer and/or cancer metastasis, including, but not is limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Specific examples of tumors associated with specific members of the ErbB family of receptor tyrosine kinases are provided hereinbelow.

ErbB-1—adrenocortical cancer, biliary cancer, cervical cancer, colorectal cancer, esophageal cancer, gallbladder cancer, gastric cancer, glioblastoma, head and neck cancer, lung cancer (non-small cell, squamous cell carcinoma, adenocarcinoma, and large cell lung cancer), pancreatic cancer, salivary gland cancer, diarrhea benign neoplasm, invasive carcinoma, skin disease, ductal carcinoma in situ, paronychia.

ErbB-2—biliary cancer, bladder cancer, breast cancer, cholangiocarcinoma, esophageal cancer, gallbladder cancer, gastric cancer, glioblastoma, ovarian cancer, pancreatic cancer, salivary gland cancer. According to a specific embodiment the cancer is breast or gastric cancer.

ErbB-3—breast cancer, lung cancer and viral leukemia.

ErbB-4—breast cancer, viral leukemia, medulloblastoma, lung cancer and mammary tumor.

In order to detect overexpression, detection is preferably made in comparison to a reference sample. Such a reference sample can be a cell of the same tissue origin of a non-affected subject.

Detection can be effected in vitro or in vivo. In vitro assays are done on isolated biological samples. Such biological samples include, but are not limited to, body fluids such as whole blood, serum, plasma, cerebrospinal fluid, urine, lymph fluids, and various external secretions of the respiratory, intestinal and genitourinary tracts, tears, saliva, milk as well as white blood cells, tissue samples (biopsies), malignant tissues, amniotic fluid and chorionic villi.

Overexpression of an ErbB receptor molecule can be at least 50% higher expression level or more (even 1,000% or more) than that in a cell of a normal tissue (non-pathogenic) of the same type and developmental stage. An example is provided by the overexpression of ErbB-2 in breast and in gastric cancer, which reaches 10-fold or higher expression relative to the corresponding normal epithelium.

Once the results are at hand they are recorded and the subject is informed. As mentioned other methods of diagnosis can be applied to corroborate the results of the present assay.

The instant aptamers can also be used in therapy such as for the treatment of cancer since as shown in FIGS. 7A-B treatment with the present aptamers causes growth arrest of cells expressing the corresponding ErbB molecule.

Thus, according to an aspect of the invention there is provided a method of killing or arresting growth of tumor cells overexpressing an ErbB receptor molecule in a subject in need thereof, the method comprising administering to the subject a therapeutically effective amount of the aptamer or multimeric aptamer described herein, thereby killing or arresting growth of the tumor cells overexpressing an ErbB receptor molecule.

Additionally, there is provided a method of treating cancer in a subject in need thereof the method comprising administering to the subject a therapeutically effective amount of the aptamer or multimeric aptamer described herein, thereby treating the cancer in the subject.

When the aptamer is conjugated to a pharmaceutical moiety, there is provided a method of delivering a pharmaceutical moiety (e.g., therapeutic or diagnostic moiety) to an ErbB expressing cell in a subject in need thereof, the method comprising administering to the subject a therapeutically effective amount of the aptamer or multimeric aptamer conjugated to the pharmaceutical moiety (e.g., therapeutic or diagnostic moiety), thereby delivering the therapeutic moiety to the subject in need thereof.

The present detection/diagnostic assays can be applied for personalized therapy. Basically, such protocols qualify a subject to treatment with the aptamers of the present invention or with any other drug which is compatible with ErbB positive marker expression. Thus once pathogenic expression of an ErbB receptor molecule is evidenced, the subject is treated with a suitable treatment regimen.

The present modes of treatments may be combined with other anti cancer treatments including chemotherapy, radiotherapy, antibody therapy. Specific examples include, but are not limited to, Cetuximab, Erlotinib, Gefitinib, Lapatinib, Panitumumab and Trastuzumab/Herceptin™. Chemotherapeutic agents for combination therapies might comprise specific anthracyclins and derivatives of platinum although other chemotherapeutic agents may be used.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

The aptamers of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the aptamers accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (aptamers) effective to prevent, alleviate or ameliorate symptoms of a disorder (e.g., aptamers) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide aptamer (the cancer e.g., gastric tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It is expected that during the life of a patent maturing from this application many relevant aptamers will be developed and the scope of the term aptamer is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Experimental Procedures

Materials

Cell lines were purchased from the American Type Culture Collection (Manassas, Va.) and grown in RPMI 1640 (N87) or DMEM/F12 (A431) (Biological Industries, Beit Haemek, Israel) supplemented with 10% foetal calf serum. Antibodies were purchased from Santa Cruz Biotechnology (Santa Cruz, Calif.). Oligonucleotides were purchased from Hylabs (Rehovot, Israel). Phycoerythrin streptavidin was from BD Biosciences.

SELEX screens

The outline of the screen relates to the so-called "One-Pot" experiment, where the whole process takes place in a single PCR-tube [Missailidis S (2003) Targeting of Antibodies using Aptamers. *Antibody engineering: methods and protocols*, ed Lo B K C (Humana Press), Vol 51, pp 547-555]. The surface of the tube was coated at 4° C. with an ErbB-2-specific, rabbit polyclonal anti-serum. Following washing and blocking (2 hrs) with 3% milk powder, cleared extracts of N87 cells (500 μg/ml; 50 μl) were added. Two hours later, the tube was incubated (37° C.; 60 minutes) with a single-stranded DNA library (1 μM; from Invitrogen) of aptamers, containing two constant primer binding regions and a 50-nucleotide random sequence (5'-ATACCAGCTT-ATTCAATT-N40-AGATAGTAAGTGCAATCT-3', SEQ ID NO: 4)[Crameri A & Stemmer W P (1993) 10(20)-fold aptamer library amplification without gel purification. *Nucleic acids research* 21(18):4410]. Unbound DNA strands were removed and PCR reagents (50 μl) were added. A fluorescein-labelled primer (1 μM; 5'-FL-ATACCAGCTT-ATTCAATT-3', SEQ ID NO: 5) was used for the leading strand, and a biotinylated primer (5'-Biotin-AGATTG-CACTTACTATCT-3', SEQ ID NO: 6) for the lagging strand. After PCR, biotinylated, double-stranded products were incubated (1 h at 4° C.) with Streptavidin-coated beads. Thereafter, the beads were washed twice, re-suspended in saline and heat-denatured at 95° C. for 5 minutes, to release fluorescein-labelled leading strands. The supernatant was collected and the biotinylated strands were removed. Fluorescence of labelled leading strands was measured, and selected aptamers were used for a new SELEX round. After four iterative selection rounds, and one counter selection round (to remove background binders), the selected aptamer sequences were subcloned into a pGEM-T vector and transformed into bacteria. After sequencing, only aptamers with shorter sequences (due to random PCR deletions) than the original random sequence in the library were selected for further characterization and functional tests. All aptamer sequences were synthesized without primers. The sequence of aptamer 2-2 is: GCAGCGGTGTGGGG, SEQ ID NO: 2.

ELISA and dot blot assays

A heterogeneous, non-competitive, direct ELISA binding assay was used to test direct binding of aptamer 2-2(t) to native ErbB-2 from N87 cell extracts. An ErbB-2-specific, polyclonal rabbit antibody (to the kinase domain) was used to coat a solid plate surface (Nunc; Langenselbold, Germany) and incubated overnight at 4° C. After three washing steps, the plate was blocked with 3% milk powder, and extracts of N87 cells were applied (at 100 μg/ml). After three additional washing steps, several concentrations of a biotinylated aptamer 2-2(t) (up to 100 nM) were allowed to bind for two hours. Once again, the plate was washed, streptavidin-HRP conjugate was applied as a secondary detection reagent. The plate was washed and tetra-methyl-benzidine substrate (Enco, Petach Tikvah, Israel) was applied to the plate. Color development was terminated after 10 minutes, with $H_2SO_4$ (2N), and light absorbance (450 nm) was measured using an ELISA reader (Lumitron, Lod, Israel). The competition assay was similarly performed with 10 nM biotinylated, trimeric aptamer 2-2(t) and different concentrations of the unlabeled aptamer 2-2(t). For dot blots, 0.2 ml extracts of N87 or A431 cells (0.1 mg protein per ml) were spotted in duplicates onto a nitrocellulose membrane. The membrane was blocked and biotinylated, monomeric and trimeric aptamers (100 nM) were applied together with 1% milk powder to avoid non-specific binding. After three washing steps, HRP-labelled streptavidin was used. The ECL detection kit (Amersham Pharmacia Biotech, Nümbrecht, Germany) was used to detect signals by chemiluminescence.

Trimerization was based on continuous linear synthesis of triplicate of the aptamer.

Regular and double immunoblotting

N87 cell extracts were resolved using gel electrophoresis, and blotted onto a first nitrocellulose membrane. The membrane was blocked with 3% milk powder, and subsequently incubated for two hours with specific aptamers (100 nM). After three washing steps, the membrane was re-blotted to a second membrane, which was blocked, incubated with HRP-labelled streptavidin, washed three times and chemiluminescence of specific bands was determined.

Pull-down assays

Biotinylated, monomeric and trimeric aptamers (1 μM), or the primer from the SELEX rounds, were incubated overnight at 4° C. with extracts from N87 or A431 cells (500 μg/ml). Streptavidin magnetic beads (10 μl; Novagen) were applied to allow pull-down and the beads were washed three times in saline. Samples were resolved using gel electrophoresis, and blotted to a nitrocellulose membrane (Rhenium, Jerusalem, Israel). The membrane was blocked with milk (3%, in saline) and an ErbB-2-specific, rabbit polyclonal antiserum specific to the kinase domain (Santa Cruz Biotechnology) was used to detect ErbB-2. After three washing steps, an HRP-labelled, secondary antibody (Jackson ImmunoResearch Laboratories, Bar Harbor, Me.) was used for colorimetric staining.

Cell proliferation assays

Cells (10,000 cells/ml) were grown for 24 h in 96-well plates in DMEM/F12 (1:1; 100 μl/well). Next, the medium was removed, and aptamers (10 μM) were applied in triplicates. The medium contained 1% serum and it was refreshed every two days with aptamer-containing medium. Cell proliferation was determined seven days later, by using an XTT proliferation assay kit (Biological Industries, Beit Haemek, Israel).

FACS analysis

N87 cancer cells were treated with trypsin, washed and incubated at 4° C. for 30 minutes with the biotinylated ErbB-2-specific aptamer 2-2(t), a trimeric primer as control (each at 1 μM), or biotin, in saline (containing 0.1% albumin). Thereafter, cells were washed and phycoerythrin streptavidin added for 30 min at 4° C. After washing, bound aptamer molecules were detected and cells analyzed using a fluorescent activated cell sorter (FACS).

In vivo experiments

Female CD-1 nude mice were injected subcutaneously with N87 cells ($5 \times 10^6$) human gastric cancer cells. Treatment with the indicated agents started seven days post inoculation, when tumors became palpable and measurable. Groups of 7 mice were injected intraperitoneally with either aptamers (40 μg/mouse) or an antibody (160 μg/mouse).

Immunofluorescence

N87 cells were plated on fibronectin-coated cover slips, twenty-four hours prior to treatment with a fluorescein-tagged aptamer. Following three days of treatment, cells were washed, permeabilized (0.03% Triton X-100) and fixed (3% paraformaldehyde). A polyclonal anti-ErbB-2 antibody (Santa-Cruz, Calif.) and a fluorescent secondary antibody (Invitrogen, Carlsbad, Calif.) were used to visualize ErbB-2. Nuclei were visualized using DAPI counterstaining. Microscopy used the DeltaVision System (Applied Precision) and a 100X/1.4 objective.

Statistical Analysis

The two-way student t-test was used to analyze differences between groups.

Example 2

Selection of Monomeric Aptamers which Display Specificity to ErbB-2

ErbB-2-specific aptamers were selected in five SELEX selection rounds from a single-stranded DNA library (see a scheme in FIG 1). Each aptamer of the library comprises two constant primer-binding regions, and a 50-nucleotide long random insert. A fluorescein-labelled PCR-primer enabled ligand quantification, following each selection round. Antibody-immobilized, native ErbB-2 protein from human N87 gastric cancer cells, which overexpress the oncogenic protein, served as a selection target. In order to test target specificity of selected aptamers, a series of assays were applied, including titration and competition tests (FIGS. 2A and 2B), as well as a double-immunoblot analysis. For this latter assay, N87 cells were lysed, extracted proteins were resolved (using gel electrophoresis) and blotted to a nitrocellulose membrane. Three selected, biotinylated aptamers, along with a control biotinylated primer from the SELEX rounds, were incubated with the membrane. To exclude non-specific interactions, a second blotting step was introduced, which electrophoretically transferred aptamer-ErbB-2 complexes to a second membrane. This second membrane was incubated with streptavidin-HRP, prior to developing a chemiluminescence signal (FIG. 3A). The results presented in FIG. 3A clearly show that all selected aptamers (B212 (SEQ ID NO: 1), 2-2 (SEQ ID NO: 2) and 2-1(SEQ ID NO: 3)) were able to specifically bind with ErbB-2. In contrast, the primer control (PR) failed to bind with ErbB-2.

In a second attempt to examine specificity, a single aptamer, denoted 2-2 (SEQ ID NO: 2), was tested in a pull-down experiment. The biotinylated aptamer, along with the biotinylated control primer, PR, were incubated with whole extracts derived from either ErbB-2-overexpressing N87 cells, or from ErbB-1-overexpressing A431 cells. After three washing steps, streptavidin magnetic beads were allowed to bind with ErbB-2-aptamer complexes. Pulled-down complexes were resolved by gel electrophoresis and blotted onto a nitrocellulose membrane. The membrane was blocked, and the aptamer-tagged ErbB-2 was detected using a kinase domain-specific rabbit polyclonal anti-serum, along with a secondary HRP-labelled antibody. This experiment demonstrated high ErbB-2 specificity of aptamer 2-2, relative to the control primer (FIG. 3B; left panel). In addition, aptamer 2-2 was also shown incapable of binding to overexpressed ErbB-1 of A431 cells (FIG. 3B; right panel). In summary, the aptamer selected (2-2; 14mer) showed high specificity to human ErbB-2. No other protein, including the closest family member of ErbB-2, namely ErbB-1, could similarly bind with the selected aptamer.

Example 3

Aptamer Multimerization and its Biological Activity

In order to enhance the avidity of the selected 2-2 aptamer, and also enable crosslinking of ErbB-2 molecules expressed on tumor cells, a trimeric version was designed. Superior binding of the trimeric aptamer was first verified by a dot blot assay. Monomeric and trimeric biotinylated aptamers were allowed to interact with spotted whole extracts of ErbB-2-overexpressing N87 cells, or extracts derived from ErbB-1-overexpressing A431 cells. Next, bound aptamers were exposed to streptavidin-HRP and chemiluminescence was measured. As shown in FIG. 4A, very faint or no binding of monomeric aptamer 2-2 was detected. On the other hand, the trimeric version of aptamer 2-2(t) clearly displayed specific binding with extracts derived from N87 cells. The relatively low level of ErbB-2 expressed by A431 cells, likely underlies the minor signal observed with these cells. Flow cytometry analyses similarly supported enhanced binding by the trimeric aptamer. Biotin-labelled trimeric aptamers 2-2(t) and PR(t), along with biotin as an additional control, were incubated with N87 cells, prior to treatment with phycoerythrin streptavidin and fluorescence-based cell sorting. As indicated by FIG. 4B, the trimeric aptamer 2-2(t) was able to efficiently bind with ErbB-2-overexpressing cells, whereas both controls (biotin and the trimeric primer) demonstrated no binding.

Next, a pull-down assay was employed to directly compare the trimeric and monomeric versions of the selected aptamer. Biotinylated aptamers 2-2(t) and PR(t) were allowed to bind extracts of either N87 or A431 cells. Streptavidin magnetic beads were applied and the aptamer-receptor complexes were first pulled-down and then resolved by using gel electrophoresis and immunoblotting. Unlike the control primer, aptamer 2-2(t) could efficiently precipitate large amounts of ErbB-2 from extracts of N87 cells, and much smaller receptor amounts were precipitated from A431 cells (FIG. 4C). Thus, in comparison to the monomeric aptamer, the trimeric version of aptamer 2-2 displayed improved binding, while preserving high specificity to ErbB-2. Conceivably, the extended length of aptamer 2-2(t) does not interfere with binding, implying that key structural elements needed for target binding remain unchanged after multimerization.

Example 4

Aptamer-Induced Internalization and Lysosomal Degradation of ErbB-2

In order to follow the fate of aptamer-bound ErbB-2 molecules, N87 cells were incubated for three days with the trimeric aptamer 2-2(t) (100 nM), and then used immunofluorescence to localize ErbB-2. Unlike untreated cells, which displayed the characteristic localization of ErbB-2 at the cell surface, aptamer-treated cells displayed no membranal signal (FIG. 5). Instead, multiple puncta of ErbB-2, which avoided the nucleus, were displayed by aptamer-treated cells. This observation proposed that aptamer-mediated crosslinking of ErbB-2 molecules, targets the oncogenic receptor to the well-studied pathway of endocytosis, culminating in delivery to lysosomes for degradation (reviewed in Zwang Y & Yarden Y (2009) Systems biology of growth factor-induced receptor endocytosis. *Traffic* 10(4): 349-363). To examine inducible degradation, N87 cells were incubated with the trimeric aptamer 2-2(t), or with the trimeric control primer PR(t), extracted at 24-hour intervals and resolved by immunoblotting. This analysis clearly showed that ErbB-2 underwent extensive degradation following treatment with the trimeric 2-2 aptamer, whereas the control primer exerted no impact on protein stability (FIG. 6A). As shown before, ErbB-2 undergoes degradation in lysosomes, once perturbed by growth factors or monoclonal antibodies (Klapper L N, Waterman H, Sela M, & Yarden Y (2000) Tumor-inhibitory antibodies to HER-2/ErbB-2 may act by recruiting c-Cbl and enhancing ubiquitination of HER-2. *Cancer research* 60(13):3384-3388; Kasprzyk P G, Song S U, Di Fiore P P, & King C R (1992) Therapy of an animal model of human gastric cancer using a combination of anti-erbB-2 monoclonal antibodies. *Cancer research* 52(10):2771-2776). Therefore, the effect of a specific inhibitor of lysosomal degradation, namely chloroquine, on ErbB-2 degradation, was tested. As shown in FIG. 6B, the drug almost completely inhibited the effect of aptamer 2-2(t) on ErbB-2 degradation. Hence, on the basis of the presented structural and functional lines of evidence, it is concluded that the trimeric aptamer 2-2(t) effectively targets ErbB-2 to intracellular degradation.

Example 5

The Trimeric Aptamer Inhibits Growth of Gastric Cancer Cells Both In Vitro and In Vivo While at the cell surface, ErbB-2 delivers strong oncogenic signals, but this does not occur when ErbB-2 is localized in intracellular compartments (Flanagan J G & Leder P (1988) neu protooncogene fused to an immunoglobulin heavy chain gene requires immunoglobulin light chain for cell surface expression and oncogenic transformation. *Proceedings of the National Academy of Sciences of the United States of America* 85(21):8057-8061). Hence, aptamer-induced internalization is expected to reduce the ability of an overexpressed ErbB-2 to deliver mitogenic and oncogenic signals in tumor cells. To test this prediction, N87 cells ($10^3$/well) were treated for seven days with either the trimeric aptamer 2-2(t) or with the trimeric primer PR(t). As demonstrated in FIG. 7A, only aptamer 2-2(t) could efficiently inhibit cell proliferation, whereas untreated control cells, as well as cells treated with the monomeric 2-2 aptamer, and cells treated with either the monomeric or trimeric versions of the control primer, reflected no significant effect on proliferation.

As a prelude for testing the effects of the trimeric aptamer in animals bearing N87 tumors the stability of aptamer 2-2(t) was determined in mouse serum. By using PCR and measuring fluorescence of aptamer-containing serum samples, it was concluded that 2-2(t) is stable for at least 48 hours, before emergence of the first signs of degradation (FIG. 8). On the basis of these results, N87 cells were implanted in CD-1 immunocompromised mice, and treatments were initiated once tumors became palpable. Mice were left untreated, or they were treated weekly for 8 times with the control PR(t) or with aptamer 2-2(t). A third group was treated with an ErbB-2-specific monoclonal antibody, mAb431, because this antibody can partially inhibit tumorigenic growth of N87 cells in mice [Ben-Kasus T, Schechter B, Lavi S, Yarden Y, & Sela M (2009) Persistent elimination of ErbB-2/HER2-overexpressing tumors using combinations of monoclonal antibodies: relevance of receptor endocytosis. *Proceedings of the National Academy of Sciences of the United States of America* 106(9):3294-3299]. In line with this, three independent experiments indicated that mAb431 significantly reduced tumor growth in comparison to untreated animals, and also relative to mice treated with the PR(t) control oligonucleotide (p<0.003; FIG. 7B). Importantly, the trimeric 2-2 aptamer consistently displayed, in all three experiments, greater anti-tumor effects than the antibody tested (p<0.0003). Moreover, the inhibitory effects exerted by mAb431 and aptamer 2-2(t) were initially quite similar, as long as the respective agents were injected, but they separated upon cessation of treatment (around day 70). This long-term difference might be attributed to either pharmacokinetics or mechanisms of action.

In summary, a consistent picture emerged from the studies performed in vitro and in animals. Accordingly, the trimeric aptamer selected on the basis of specificity to ErbB-2 can effectively suppress growth of N87 human gastric cells, and this effect exceeds the inhibition observed in a xenograft model treated with a mAb to ErbB-2. Predictably, combining the trimeric aptamer with chemotherapy, antibodies or other drugs, along with optimizing schedule of delivery, might enhance the anti-tumor activity of the aptamer, thereby offer a new strategy to treat ErbB-2 overexpressing human cancer.

DISCUSSION

This study developed an aptamer with specificity to ErbB-2/HER2, a master regulator of a signalling network essential for progression of several different types of carcinoma, including one subtype of gastric cancer. After selecting several aptamers it was decided, based on specificity tests, to concentrate on one, aptamer 2-2, which was subsequently multimerized to form aptamer 2-2(t). Aptamer multimerization served two purposes: First, enhancing the avidity of binding to ErbB-2, and second: crosslinking the receptor on the surface of living cells. Accordingly, on the one hand it was demonstrated that the trimeric aptamer 2-2(t) is endowed with improved binding to ErbB-2, in comparison to the monomeric version. On the other hand, by using immunofluorescence and western blotting, it was confirmed that aptamer 2-2(t) can induce translocation of ErbB-2 from the plasma membrane to cytoplasmic vesicles (FIG. 5). Furthermore, the ability of aptamer 2-2(t) to accelerate degradation of the oncogenic target was validated using immunoblot analyses (FIGS. 6A-B). In light of the observation that the degradation machinery was reversed by an inhibitor of lysosomal hydrolases (i.e., chloroquine), this set of results leads to the assumption that the biological activity of aptamer 2-2(t) relates to a functional internalization process.

The trimeric aptamer, in comparison to the monomer, is also characterized by superior anti-proliferative capacity, when tested in vitro on gastric cancer cells overexpressing ErbB-2 (FIG. 7A). The lack of anti-proliferative activity of the respective monomer might be related to its lower binding, or inability to crosslink ErbB-2 molecules on the cell surface Importantly, the inhibitory effect of the trimeric aptamer extended to a xenograft model that used immunocompromised mice. This observation not only demonstrated in vivo relevance, but it also favored a non-immunological mechanism. Notably, aptamer 2-2(t) displayed superior anti-tumor activity in comparison to a monoclonal anti-ErbB-2 antibody. Antibody 431 engages the epitope targeted by Trastuzumab, the humanized antibody approved for treatment of breast and gastric cancer. Interestingly, mAb431 inhibited tumor growth more efficiently during the first weeks of treatment, whereas the effect of aptamer 2-2(t) was more sustained, an observation which relates to differential stability or clearance of the drugs. Another difference entails the ability of mAb431 to recruit, at least to some extent, the immune system. It is generally accepted that antibody-dependent cellular cytotoxicity (ADCC) plays a major role in immunotherapy, such as in protocols that make use of Trastuzumab. However, the growth-inhibitory activities of aptamer 2-2(t) observed in vitro and in animals, as well as the chemical nature of a DNA aptamer, exclude immunological mechanisms of action.

In summary, this study offers a new, generally applicable strategy to target cell surface receptors in the context of cancer therapy. Accordingly, aptamers are selected on the basis of effective binding to the surface receptor or transporter of interest. Once target specificity is validated, the aptamer might be converted into a linear oligomer, capable of multi-valent binding to the target. In the next step, the ability of the extended aptamer to translocate the target molecule from the cell surface to intracellular compartments (e.g., endosomes or lysosomes) is verified, and animal models are employed to demonstrate anti-tumor effects in vivo. Combination treatments with chemotherapeutics, biologics (e.g., antibodies and decoy receptors), as well as therapeutic radiation, might augment clinical efficacy, thereby represent a future alternative to conventional therapies. In addition, because of their target specificity and versatile modifications, aptamers might be harnessed as carriers of toxic loads. This has been demonstrated by applying RNA aptamers and drug-encapsulated nanoparticles on prostate tumor xenografts, which exemplifies yet another potential application of the anti-ErbB-2 aptamer identified in this study.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited throughout the Application

1. Yarden Y & Sliwkowski M X (2001) Untangling the ErbB signalling network. *Nat Rev Mol Cell Biol* 2(2):127-137.
2. Ciardiello F & Tortora G (2008) EGFR antagonists in cancer treatment. *The New England journal of medicine* 358(11):1160-1174.
3. Stoltenburg R, Reinemann C, & Strehlitz B (2007) SELEX—a (r)evolutionary method to generate high-affinity nucleic acid ligands. *Biomolecular engineering* 24(4):381-403.
4. Tuerk C & Gold L (1990) Systematic evolution of ligands by exponential enrichment: RNA ligands to bacteriophage T4 DNA polymerase. *Science* 249(4968):505-510.
5. Ellington A D & Szostak J W (1990) In vitro selection of RNA molecules that bind specific ligands. *Nature* 346 (6287):818-822.
6. Tombelli S, Minunni M, & Mascini M (2005) Analytical applications of aptamers. *Biosensors & bioelectronics* 20(12):2424-2434.
7. Guo K T, Ziemer G, Paul A, & Wendel H P (2008) CELL-SELEX: Novel perspectives of aptamer-based therapeutics. *International journal of molecular sciences* 9(4):668-678.
8. Famulok M & Mayer G (2011) Aptamer modules as sensors and detectors. *Accounts of chemical research* 44(12):1349-1358.
9. Bates P J, Kahlon J B, Thomas S D, Trent J O, & Miller D M (1999) Antiproliferative activity of G-rich oligonucleotides correlates with protein binding. *The Journal of biological chemistry* 274(37):26369-26377.
10. Li N, Nguyen H H, Byrom M, & Ellington A D (2011) Inhibition of Cell Proliferation by an Anti-EGFR Aptamer. *PloS one* 6(6):e20299.
11. Dastjerdi K, Tabar G H, Dehghani H, & Haghparast A (2011) Generation of an enriched pool of DNA aptamers for an HER2-overexpressing cell line selected by Cell SELEX. *Biotechnology and applied biochemistry* 58(4): 226-230.
12. Esposito C L, et al. (2011) A neutralizing RNA aptamer against EGFR causes selective apoptotic cell death. *PloS one* 6(9):e24071.
13. Kim M Y & Jeong S (2011) In vitro selection of RNA aptamer and specific targeting of ErbB2 in breast cancer cells. *Nucleic acid therapeutics* 21(3):173-178.
14. Chen C H, Chemis G A, Hoang V Q, & Landgraf R (2003) Inhibition of heregulin signaling by an aptamer that preferentially binds to the oligomeric form of human epidermal growth factor receptor-3. *Proceedings of the National Academy of Sciences of the United States of America* 100(16):9226-9231.
15. Dassie J P, et al. (2009) Systemic administration of optimized aptamer-siRNA chimeras promotes regression of PSMA-expressing tumors. *Nature biotechnology* 27(9):839-849.
16. Zwang Y & Yarden Y (2009) Systems biology of growth factor-induced receptor endocytosis. *Traffic* 10(4):349-363.
17. Klapper L N, Waterman H, Sela M, & Yarden Y (2000) Tumor-inhibitory antibodies to HER-2/ErbB-2 may act by recruiting c-Cbl and enhancing ubiquitination of HER-2. *Cancer research* 60(13):3384-3388.
18. Kasprzyk P G, Song S U, Di Fiore P P, & King C R (1992) Therapy of an animal model of human gastric cancer using a combination of anti-erbB-2 monoclonal antibodies. *Cancer research* 52(10):2771-2776.
19. Flanagan J G & Leder P (1988) neu protooncogene fused to an immunoglobulin heavy chain gene requires immunoglobulin light chain for cell surface expression and oncogenic transformation. *Proceedings of the National Academy of Sciences of the United States of America* 85(21):8057-8061.
20. Ben-Kasus T, Schechter B, Lavi S, Yarden Y, & Sela M (2009) Persistent elimination of ErbB-2/HER2-overexpressing tumors using combinations of monoclonal antibodies: relevance of receptor endocytosis. *Proceedings of the National Academy of Sciences of the United States of America* 106(9):3294-3299.
21. Friedman L M, et al. (2005) Synergistic down-regulation of receptor tyrosine kinases by combinations of mAbs: implications for cancer immunotherapy. *Proceedings of the National Academy of Sciences of the United States of America* 102(6):1915-1920.
22. Spangler J B, et al. (2010) Combination antibody treatment down-regulates epidermal growth factor receptor by inhibiting endosomal recycling. *Proceedings of the National Academy of Sciences of the United States of America* 107(30):13252-13257.
23. Clynes R A, Towers T L, Presta L G, & Ravetch J V (2000) Inhibitory Fc receptors modulate in vivo cytoxicity against tumor targets. *Nat Med* 6(4):443-446.
24. Farokhzad O C, et al. (2006) Targeted nanoparticle-aptamer bioconjugates for cancer chemotherapy in vivo. *Proceedings of the National Academy of Sciences of the United States of America* 103(16):6315-6320.
25. Missailidis S (2003) Targeting of Antibodies using Aptamers. *Antibody engineering: methods and protocols*, ed Lo B K C (Humana Press), Vol 51, pp 547-555.
26. Crameri A & Stemmer W P (1993) 10(20)-fold aptamer library amplification without gel purification. *Nucleic acids research* 21(18):4410.

What is claimed is:

1. An isolated aptamer comprising a nucleic acid sequence selected from the group consisting of SEQ ID NO: 1, 2 and 3.

2. A multimeric aptamer comprising a plurality of monomers, wherein at least one monomer of said plurality of monomers is the aptamer of claim 1.

3. The aptamer of claim 1, being attached to a detectable moiety.

4. The aptamer of claim 1, being attached to a therapeutic moiety.

5. A pharmaceutical composition comprising as an active ingredient the aptamer of claim 1 and a pharmaceutically acceptable carrier or diluent.

6. A method of detecting an expression of an ErbB receptor molecule on a cell, the method comprising:
   (a) contacting the cell or a preparation thereof with the aptamer of claim 1 under conditions which allow complex formation between said ErbB receptor molecule and the aptamer;
   (b) detecting a presence or level of said complex, thereby detecting expression of said ErbB receptor molecule.

7. A method of delivering a therapeutic moiety to an ErbB expressing cell in a subject in need thereof, the method comprising administering to the subject a therapeutically effective amount of the aptamer of claim 4, thereby delivering the therapeutic moiety to the subject in need thereof.

8. A method of killing or arresting growth of tumor cells overexpressing an ErbB receptor molecule in a subject in need thereof, the method comprising administering to the subject a therapeutically effective amount of the aptamer of claim 1, thereby killing or arresting growth of the tumor cells overexpressing an ErbB receptor molecule.

9. A method of treating cancer in a subject in need thereof the method comprising administering to the subject a therapeutically effective amount of the aptamer of claim 1, thereby treating the cancer in the subject.

10. A multimeric aptamer as set forth in SEQ ID NO: 7.

11. The multimeric aptamer of claim 2, wherein said multimeric aptamer is devoid of spacers between said plurality of monomers.

* * * * *

SEQUENCE LISTING

<160> NUMBER OF SEQ ID NOS: 7

<210> SEQ ID NO 1
<211> LENGTH: 15
<212> TYPE: DNA

```
<213> ORGANISM: Artificial sequence
<220> FEATURE:
<223> OTHER INFORMATION: B212 aptamer

<400> SEQUENCE: 1
gggctggggt gacgt                                                          15

<210> SEQ ID NO 2
<211> LENGTH: 14
<212> TYPE: DNA
<213> ORGANISM: Artificial sequence
<220> FEATURE:
<223> OTHER INFORMATION: 2-2 aptamer

<400> SEQUENCE: 2
gcagcggtgt gggg                                                           14

<210> SEQ ID NO 3
<211> LENGTH: 15
<212> TYPE: DNA
<213> ORGANISM: Artificial sequence
<220> FEATURE:
<223> OTHER INFORMATION: 2-1 aptamer

<400> SEQUENCE: 3
gggctggtgt ggcgg                                                          15

<210> SEQ ID NO 4
<211> LENGTH: 76
<212> TYPE: DNA
<213> ORGANISM: Artificial sequence
<220> FEATURE:
<223> OTHER INFORMATION: A single-stranded DNA aptamers library sequence
<220> FEATURE:
<221> NAME/KEY: misc_feature
<222> LOCATION: (19)..(58)
<223> OTHER INFORMATION: n is a, c, g, or t

<400> SEQUENCE: 4
ataccagctt attcaattnn nnnnnnnnnn nnnnnnnnnn nnnnnnnnnn nnnnnnnnag         60
atagtaagtg caatct                                                         76

<210> SEQ ID NO 5
<211> LENGTH: 18
<212> TYPE: DNA
<213> ORGANISM: Artificial sequence
<220> FEATURE:
<223> OTHER INFORMATION: 5' fluorescein labelled oligonucleotide

<400> SEQUENCE: 5
ataccagctt attcaatt                                                       18

<210> SEQ ID NO 6
<211> LENGTH: 18
<212> TYPE: DNA
<213> ORGANISM: Artificial sequence
<220> FEATURE:
<223> OTHER INFORMATION: 5'-Biotin conjugated oligonucleotide

<400> SEQUENCE: 6
agattgcact tactatct                                                       18

<210> SEQ ID NO 7
<211> LENGTH: 42
<212> TYPE: DNA
<213> ORGANISM: Artificial sequence
```

```
<220> FEATURE:
<223> OTHER INFORMATION: Multimeric 2-2 aptamer

<400> SEQUENCE: 7
gcagcggtgt gggggcagcg gtgtgggggc agcggtgtgg gg                42
```